US00PP27740P2

(12) United States Plant Patent
Norden et al.

(10) Patent No.: US PP27,740 P2
(45) Date of Patent: Mar. 7, 2017

(54) BLUEBERRY PLANT NAMED 'PATRECIA'

(50) Latin Name: ***Vaccinium corymbosum* L.**
Varietal Denomination: Patrecia

(71) Applicant: Florida Foundation Seed Producers, Inc., Marianna, FL (US)

(72) Inventors: David E. Norden, Archer, FL (US); Alto Straughn, Gainesville, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 0 days.

(21) Appl. No.: 14/998,937

(22) Filed: Mar. 7, 2016

(51) Int. Cl.
*A01H 5/08* (2006.01)

(52) U.S. Cl.
USPC ..... Plt./157

(58) Field of Classification Search
USPC ..... Plt./157
See application file for complete search history.

(56) References Cited

U.S. PATENT DOCUMENTS

| | | | |
|---|---|---|---|
| PP10,675 | P | 11/1998 | Lyrene |
| PP12,165 | P2 | 10/2001 | Lyrene |
| PP16,404 | P3 | 4/2006 | Lyrene |
| PP26,312 | P2 | 1/2016 | Lyrene et al. |
| PP26,313 | P2 | 1/2016 | Lyrene et al. |
| PP26,523 | P3 | 3/2016 | Lyrene |
| PP26,679 | P2 | 5/2016 | Lyrene et al. |
| 2015/0237775 | P1 | 8/2015 | Lyrene |
| 2015/0237776 | P1 | 8/2015 | Lyrene |

OTHER PUBLICATIONS

U.S. Appl. No. 14/998,938, filed Mar. 7, 2016, Lyrene.

*Primary Examiner* — June Hwu
(74) *Attorney, Agent, or Firm* — Dentons US LLP

(57) ABSTRACT

'Patrecia' is a new and distinct southern highbush blueberry (*Vaccinium corymbosum* L.) variety distinguished by a low chilling requirement, upright-spreading growth habit, and early maturing, firm, juicy fruit that are sweet with balanced acidity.

5 Drawing Sheets

Latin name of the genus and species of the plant claimed: *Vaccinium corymbosum* L.

Variety denomination: 'Patrecia'.

BACKGROUND OF THE INVENTION

The present invention relates to a new and distinct hybrid variety of southern highbush blueberry (*Vaccinium corymbosum* L.) named 'Patrecia'. 'Patrecia' is a blueberry clone distinguished by its low chilling requirement, vigorous, upright-spreading bush habit, and large, firm berries that ripen from mid-April through May when grown as a deciduous plant in north central Florida and south Georgia. Several thousand plants of 'Patrecia' have been propagated by softwood stem cuttings in Waldo, Fla., and the resulting plants have all been phenotypically indistinguishable from the original plant. Contrast is made to 'Emerald' (U.S. Plant Pat. No. 12,165), an important variety widely planted in the southeastern United States. The claimed plant is important because it has a more upright-spreading growth habit, and has larger, sweeter fruit than 'Emerald'. 'Patrecia' blooms later and fruit matures earlier than that of 'Emerald'.

'Patrecia' originated as a seedling from a cross made in February 2007 between 'Star' (U.S. Plant Pat. No. 10,675) as the female (seed) parent and 'Springhigh' (U.S. Plant Pat. No. 16,404) as the male (pollen) parent. The seedling was planted in the field in May 2008 and the first fruit were evaluated in April 2009. After the first evaluation, in the spring of 2009, 'Patrecia' was first asexually propagated by softwood stem cuttings in Waldo, Fla., and multiple experimental test plots were established as part field plantings in Waldo and Windsor, Fla., in 2010 through 2012. Based on the growth, yield, and fruit quality of these plots, 'Patrecia' was repropagated by softwood stem cuttings and experimental test plots up to 500 plants were established near Homerville, Ga. in 2013. These plots have been observed during flowering and ripening each year, and no mutations or off-type plants have been observed.

'Patrecia' differs from the parent 'Star' (U.S. Plant Pat. No. 10,675) in that 'Patrecia' has a more spreading growth habit, and has more numerous, larger berries that mature earlier. 'Patrecia' differs from the parent 'Springhigh' (U.S. Plant Pat. No. 16,404) in that 'Patrecia' has a more spreading growth habit, and has larger, firmer fruit. 'Patrecia' differs from the commercial variety 'Emerald' (U.S. Plant Pat. No. 12,165), an important variety widely planted in the southeastern United States, in that 'Patrecia' has a more upright-spreading growth habit and blooms later. 'Patrecia' berries ripen earlier and are larger and sweeter than 'Emerald' berries.

SUMMARY OF THE INVENTION

Blueberry variety 'Patrecia' exhibits outstanding and distinguishing characteristics when grown under normal horticultural practices in Florida, including:

(1) a low chilling requirement, particularly for the flower buds;
(2) a vigorous, upright-spreading growth habit;
(3) early ripening (50% ripe berries in North Florida around April 20); and
(4) firm, large, sweet berries.

BRIEF DESCRIPTION OF THE DRAWINGS

The accompanying photographs show typical bush, flower, and fruit characteristics for 'Patrecia'. Colors shown are as true as can be reasonably reproduced by photographic procedures and may differ from those cited in the detailed description, which accurately describes the colors of 'Patrecia'.

DETAILED BOTANICAL DESCRIPTION

Figure 1:
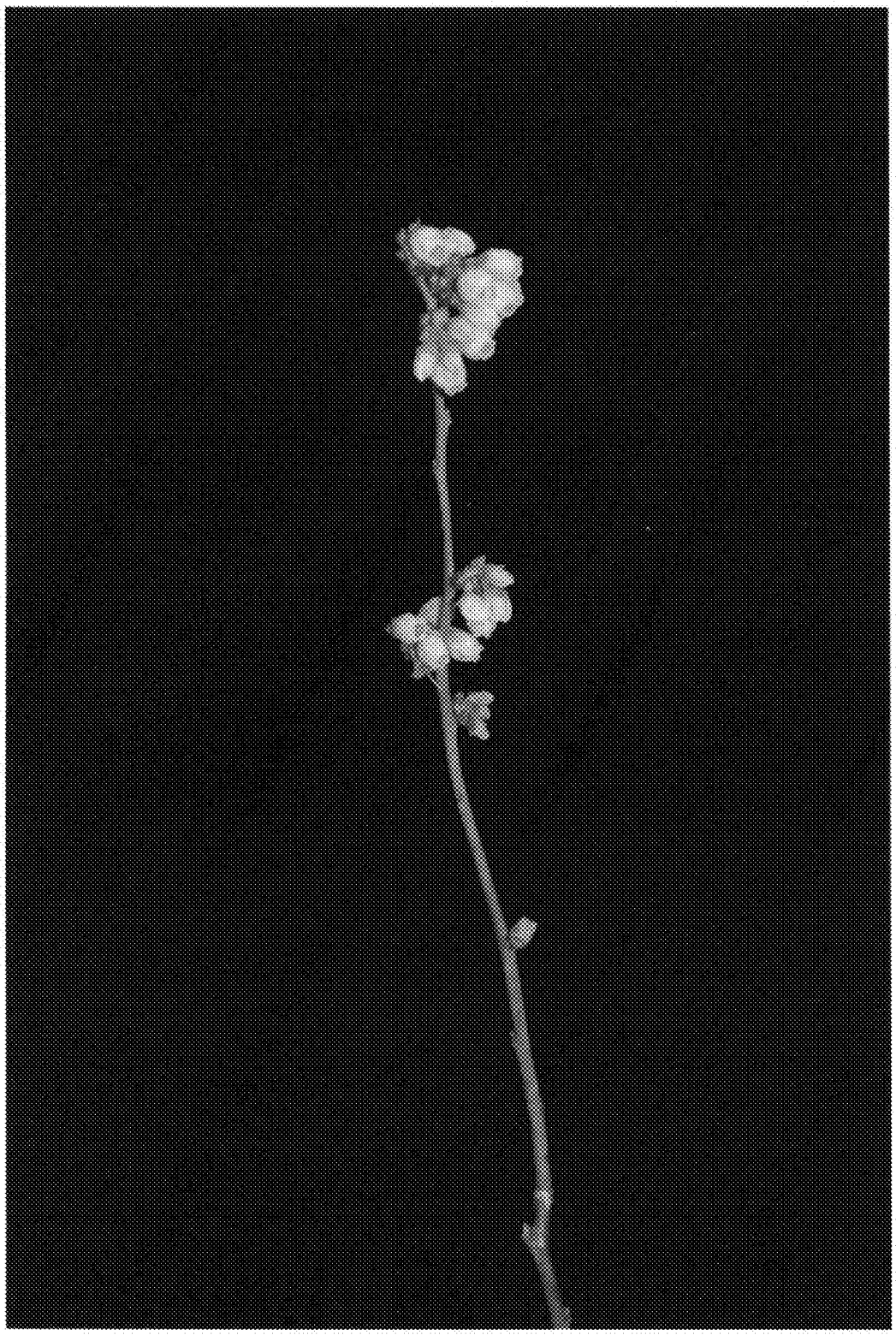
FIG. 1—Shows several clusters of opening 'Patrecia' flowers.
Figure 2:
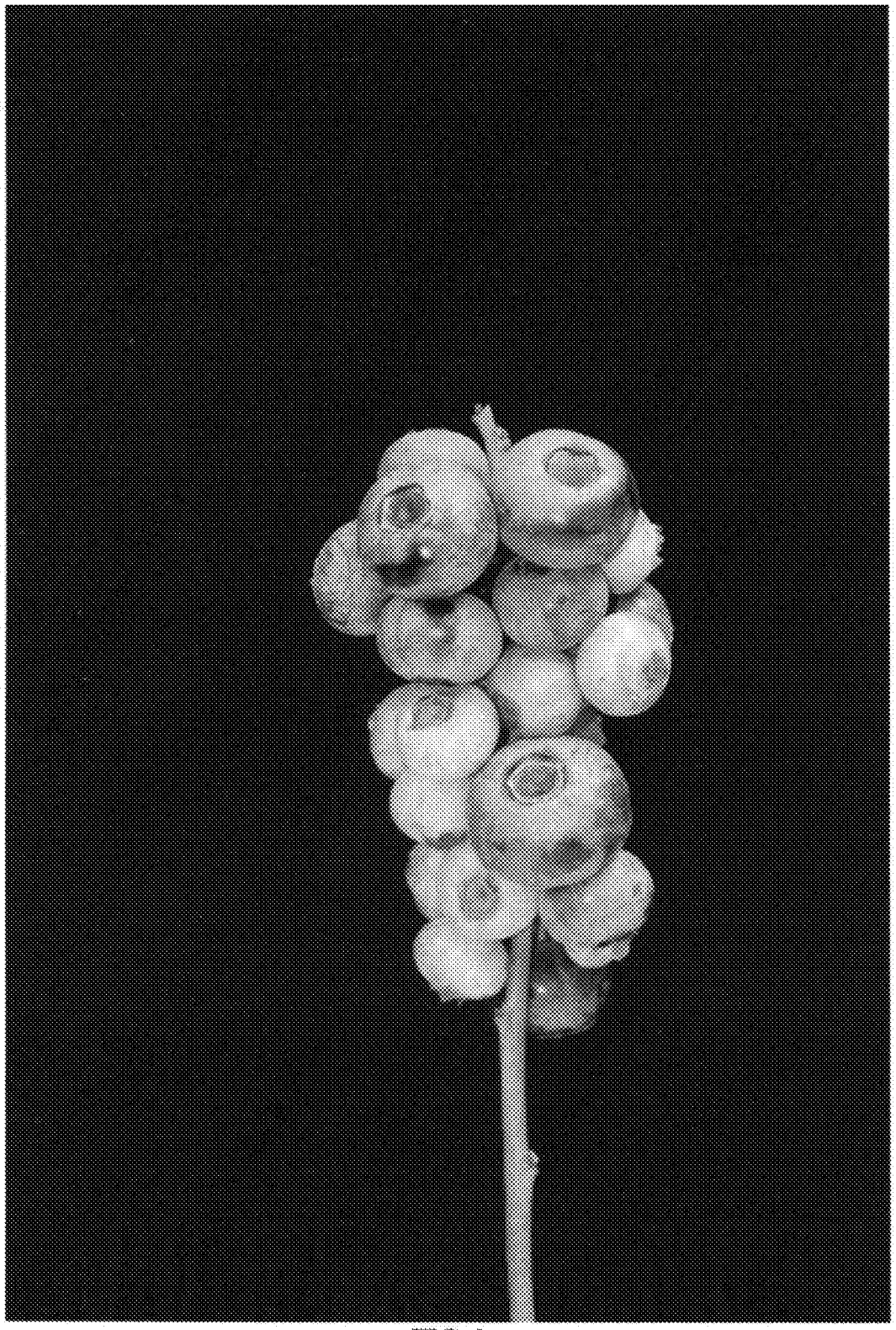
FIG. 2—Shows clusters of 'Patrecia' berries during the fruit ripening season.
Figure 3:
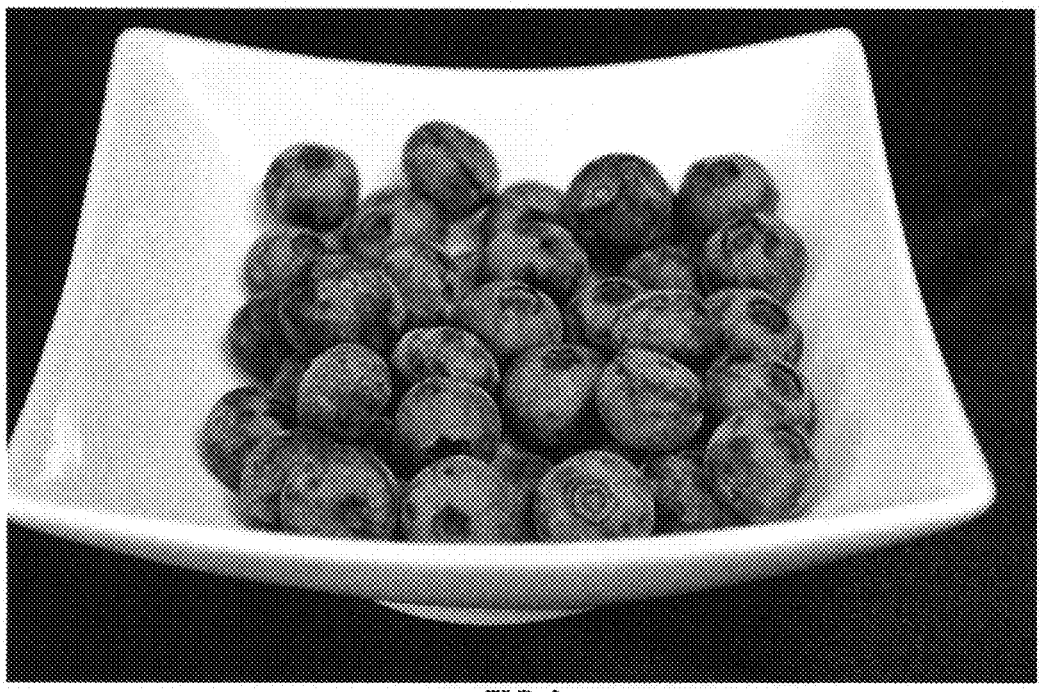
FIG. 3—Shows a close-up of harvested 'Patrecia' berries.
Figure 4:
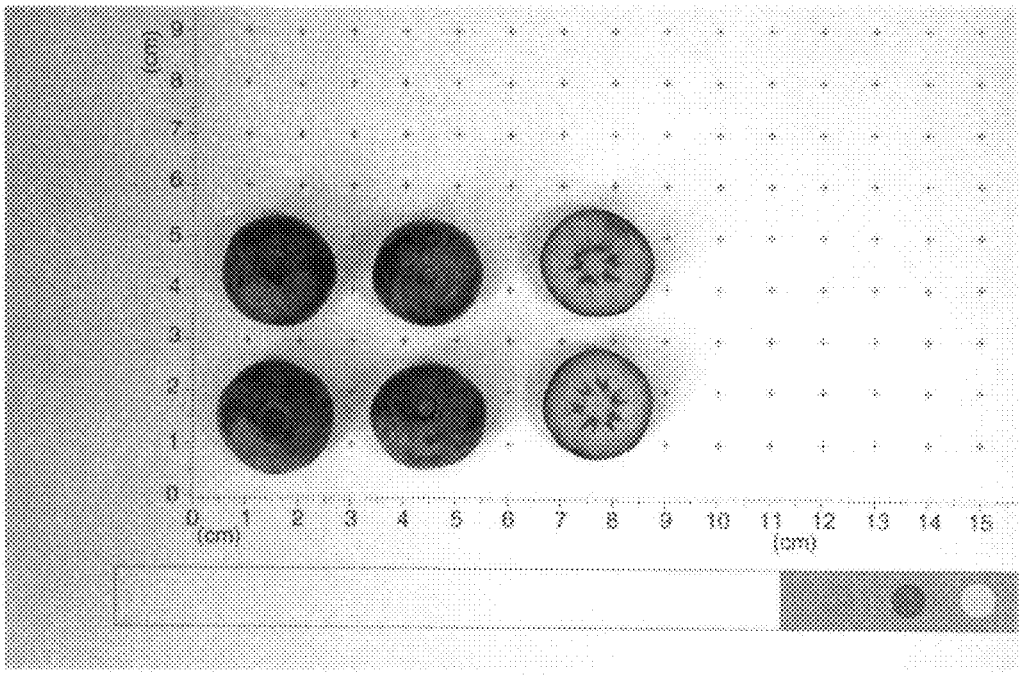
FIG. 4—Shows a close-up of mature 'Patrecia' fruit with a scale bar.
Figure 5:
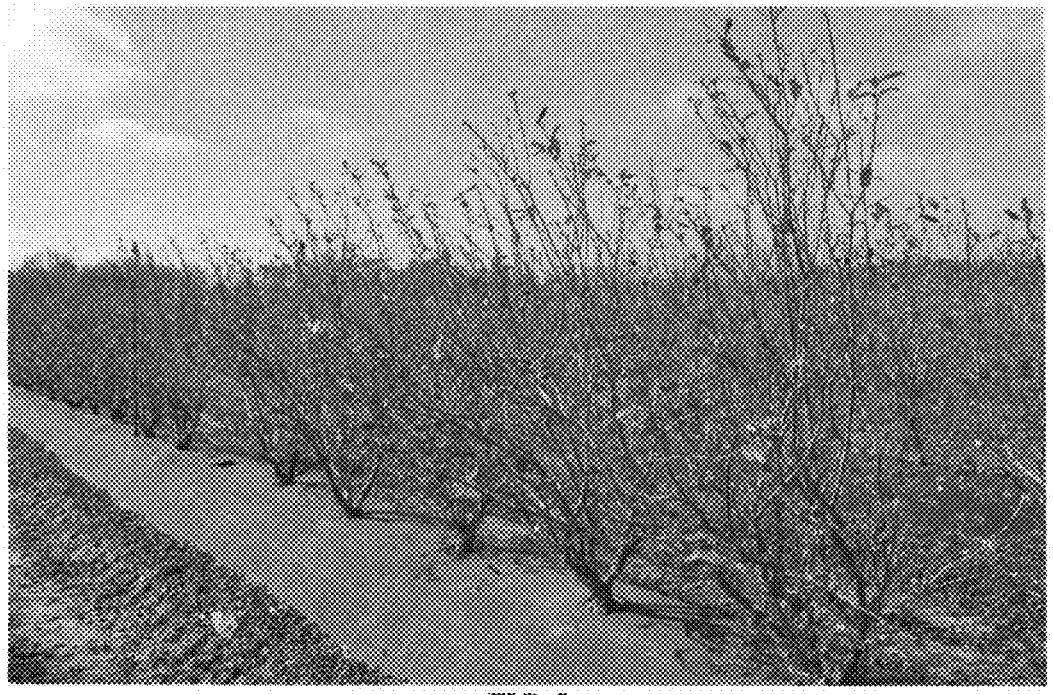
FIG. 5—Shows several three-year-old 'Patrecia' plants in February with the vigorous, upright-spreading plant architecture visible.

The following detailed description sets forth the distinctive characteristics of 'Patrecia'. The data that define these characteristics were collected from asexual reproductions carried out in Florida. The plant history was taken on a plot of 150 three-year-old plants growing in a commercial field near Windsor, Fla. Certain characteristics may vary with plant age. 'Patrecia' has not been observed under all possible environmental conditions, and the measurements given may vary when grown in different environments. Where means are given, the sample size was 20. Color descriptions are based on The Royal Horticultural Society (R.H.S.) Colour Chart by The Royal Horticultural Society, London, Fifth Edition, 2007. When the RHS color designations differ from the accompanying photographs, the RHS color designations are accurate.

PHENOTYPIC DESCRIPTION OF *VACCINIUM CORYMBOSUM* L. ('PATRECIA')

Plant:

*Plant vigor*.—High. Vigor is similar to that of 'Emerald' (U.S. Plant Pat. No. 12,165).

*Growth habit*.—Upright-spreading.

*Plant height*.—1.9 m on average for a 4-year-old plant.

*Plant spread*.—1.7 m on average for a 4-year-old plant.

*Flower bud density (number) along flowering twigs in January*.—Medium.

*Twigginess*.—Medium.

*Tendency toward evergreenness*.—Low.

*Productivity*.—In northeast Florida, 'Patrecia' produces approximately 2-3 kg per season from plants 3 years or older.

*Chilling requirement*.—300 hours below 7° C., 'Patrecia' has performed poorly when receiving less than 300 hours.

*Cold hardiness*.—'Patrecia' has not been grown in temperate climates with extremely cold winter temperatures. Plants have survived winter freezes of −5° C. with minimal damage.

*Ease of propagation*.—'Patrecia' has only been propagated from softwood stem cuttings, where the rooting percentage has greater than 80% and comparable to other varieties.

Trunk and branches:

*Suckering tendency*.—Low. Three-year-old plants typically have 5 or more major canes arising from a crown 30 cm in diameter.

*Surface texture (of strong, 6-month-old shoots observed in January)*.—Smooth.

*Surface texture (of 3-year-old and older wood)*.—Rough.

*Internode length (strong, upright shoots measured in June)*.—Mean of 12.3 mm.

*Average length of new-growth stems*.—20 cm, measured in Late August, following May pruning.

*Color of new-growth stems*.—142B.

*Color of 1-year-old wood*.—151B.

*Color of 3-year-old exfoliating canes*.—197C.

Leaves:

*Leaf length including petiole*.—64 mm on average.

*Width of leaf at widest point*.—27 mm on average.

*Leaf shape*.—Elliptic.

*Leaf margin*.—Entire.

*Leaf apex shape*.—Acute.

*Leaf base shape*.—Cuneate.

*Color of mature leaf, upper surface*.—146B.

*Color of mature leaf, lower surface*.—146C.

*Pubescence*.—Upper surface of leaves: Absent. Lower surface of leaves: Absent. Margins: Absent.

*Timing of vegetative bud burst (early, medium, late)*.—Medium.

*Relative time of leafing versus flowering*.—When not treated with hydrogen cyanamide in mid-winter, leafing occurs after flowering.

Flowers:

*Arrangement*.—Flowers are arranged alternately along a short, leafless, deciduous branch.

*Fragrance*.—None.

*Shape*.—Urceolate.

*Flowering period*.—Mid-season.

*Time of beginning of flowering*.—Mid-Season (compared to all southern highbush blueberry cultivars).

*Cluster (tight, medium, loose)*.—Medium.

*Number of flowers per cluster*.—Mean of 5.7.

*Pedicel*.—Length at time of anthesis: Mean of 3.9 mm. Color at time of anthesis: Yellow-green 145B. Average length — 4 mm.

*Peduncle*.—Length at time of anthesis: Highly variable, mean of 8.7 mm. Color at time of anthesis: Green-yellow 1C with Red 46A on sun-exposed side. Average length — 5 mm.

*Calyx*.—Surface texture: Smooth. Diameter: Mean of 5.6 mm. Color (outer surface, visible at the time of anthesis without removing the corolla tube): Green 137C to Green 138C on tips of calyx lobes.

*Corolla*.—Diameter: Mean of 6.4 mm. Length (from pedicel attachment point to corolla tip excluding the pedicel): Mean of 8.6 mm. Aperture diameter: Mean of 3.7 mm. Texture: Smooth. Color: White 155C. Anthocyanin coloration in corolla tube — Absent.

Reproductive organs:

*Style*.—Length (top of ovary to stigma tip): Mean of 7.6 mm. Color: Yellow-green 151A. Location of tip of stigma relative to lip of the corolla — Stigma tip is approximately even with the corolla lip.

*Anthers*.—Color: Greyed-orange 164A. Pollen — Abundance of shed: High. Pollen germination: Typically greater than 90%. Color: Yellow-white 158B.

*Self-fruitfulness*.—Low to medium. Planting in field configurations that promote cross fertilization with other southern highbush varieties is recommended for all southern highbush blueberry plants grown in Florida.

Fruit:

*Mean date of* 50% *harvest in Windsor, Fla*..—April 20.

*Diameter of calyx aperture on mature berry*.—Mean of 6.6 mm.

*Size and shape of calyx lobes on mature berry*.—Absent to very small, incurving. Shallow calyx basin.

*Pedicel length on ripe berry*.—Mean of 7.3 mm.

*Detachment force for ripe berries* (*easy, medium, hard*) .—Medium.

*Fruit cluster density* (*sparse, medium, dense*).—Medium.

*Number of berries per cluster*.—Mean of 5.4.

*Fruiting type*.—On one-year-old and current season's shoots.

Berry:

*Cluster* (*tight, medium, loose*).—Medium.

*Weight* (*on well-pruned plants*).—Mean of 3.5 g.

*Height*.—Mean of 13.6 mm.

*Width*.—Mean of 19.8 mm.

*Shape*.—Oblate.

*Surface color of mature berries ripe on the plant*.—Violet-blue 98D.

*Intensity of fruit bloom*.—Medium.

*Surface color of ripe berry after polishing*.—Black 203C.

*Immature berry color, with bloom*.—Yellow-green 147D.

*Immature berry color without bloom*.—Yellow-green N144A.

*Flesh color*.—NN 155 A.

*Surface wax*.—Medium to high. The surface wax on 'Patrecia' has only medium persistence.

*Pedicel scar*.—Small and dry. Mean of 3.2 mm.

*Firmness*.—Firm.

*Flavor*.—Sweet with balanced acidity.

*Intensity of fruit sweetness*.—Medium.

*Intensity of fruit acidity*.—Medium.

*Texture*.—Juicy, medium seeds, and no stone cells present.

*Fruit storage quality*.—Freshly-picked berries were stored for 2 weeks at 2° C. with no decay.

Seeds:

*Color of dried seeds*.—Greyed-orange N167A.

*Weight of well-developed dried seed*.—Mean of 0.6 mg.

*Length of well-developed dried seed*.—Mean of 2.0 mm.

*Width of well-developed dried seed*.—Mean of 1.1 mm.

Use: 'Patrecia' produces southern highbush blueberries suitable for both the fresh and processed fruit markets.

Resistance to diseases, insects, and mites: 'Patrecia' has grown vigorously and shows excellent bush survival in the field. It appears to be tolerant to stem blight (*Botryosphaeria* spp.) and root rot (*Phytophthora cinnamons*), with very few young plants dying soon after planting. The reaction of 'Patrecia' to the various fungal species that cause summer leaf spots is typical of other southern highbush varieties, and fungicide applications may be needed after harvest to reduce foliar diseases and retain leaves into the fall for maximum flower bud set. Similarly, susceptibility to typical blueberry insect and mite pathogens such as spotted wing drosophila (*Drosophila suzukii*), blueberry gall midge (*Dasineura oxycoccana*) and blueberry bud mite (*Acalitus vaccini*) is similar to other southern highbush cultivars.

What is claimed is:

1. A new and distinct variety of southern highbush blueberry plant named 'Patrecia', as illustrated and described herein.

* * * * *